(12) United States Patent
Avni

(10) Patent No.: US 8,875,705 B2
(45) Date of Patent: Nov. 4, 2014

(54) PROTOCOL AND METHODS FOR PULSATING DRUG DELIVERY

(75) Inventor: Yuval Avni, Tel Aviv (IL)

(73) Assignee: Respinova Ltd., Herzliya Pituach (IL)

( * ) Notice: Subject to any disclaimer, the term of this patent is extended or adjusted under 35 U.S.C. 154(b) by 651 days.

(21) Appl. No.: 13/122,631

(22) PCT Filed: Oct. 11, 2009

(86) PCT No.: PCT/IL2009/000961
§ 371 (c)(1),
(2), (4) Date: Apr. 5, 2011

(87) PCT Pub. No.: WO2010/038233
PCT Pub. Date: Apr. 8, 2010

(65) Prior Publication Data
US 2011/0180067 A1    Jul. 28, 2011

Related U.S. Application Data

(60) Provisional application No. 61/109,218, filed on Oct. 29, 2008.

(51) Int. Cl.
*A61M 16/16* (2006.01)
*A61M 16/00* (2006.01)
*A61M 16/12* (2006.01)
*A61M 11/02* (2006.01)

(52) U.S. Cl.
CPC ....... *A61M 16/00* (2013.01); *A61M 2205/3561* (2013.01); *A61M 16/0006* (2013.01); *A16M 15/00* (2013.01); *A61M 16/127* (2013.01); *A61M 16/0009* (2013.01); *A61M 16/0066* (2013.01); *A61M 11/02* (2013.01); *A61M 2205/502* (2013.01); *A61M 2205/07* (2013.01); *A61M 2205/103* (2013.01); *A61M 2205/8206* (2013.01)

USPC ........... 128/204.18; 128/200.24; 128/205.24; 251/281; 251/283; 251/304

(58) Field of Classification Search
None
See application file for complete search history.

(56) References Cited

U.S. PATENT DOCUMENTS

| | | | | |
|---|---|---|---|---|
| 3,972,327 A * | 8/1976 | Ernst et al. | ............... | 128/204.21 |
| 4,519,387 A * | 5/1985 | Durkan et al. | ........... | 128/204.23 |
| 4,592,349 A * | 6/1986 | Bird | ........................ | 128/204.25 |
| 5,452,714 A * | 9/1995 | Anderson et al. | ........ | 128/205.11 |
| 6,349,724 B1 * | 2/2002 | Burton et al. | ............. | 128/204.18 |
| 6,427,690 B1 * | 8/2002 | McCombs et al. | ........ | 128/204.26 |
| 6,708,691 B1 * | 3/2004 | Hayek | ....................... | 128/205.24 |
| 2003/0192545 A1 * | 10/2003 | Truitt et al. | .............. | 128/204.18 |
| 2008/0000477 A1 * | 1/2008 | Huster et al. | ............. | 128/204.23 |
| 2008/0190421 A1 * | 8/2008 | Zitting | ..................... | 128/200.24 |

* cited by examiner

Primary Examiner — Tan-Uyen T Ho
Assistant Examiner — Eric Bryant
(74) Attorney, Agent, or Firm — The Law Office of Michael E. Kondoudis

(57) ABSTRACT

An air delivery device (ADD) for applying fluid pressure pulses (FPP) to the mouth cavity of a patient at a predetermined frequency according to a protocol The ADD, comprises: a) an air blower for blowing air into a pressure chamber via a first opening (inlet); b) airflow occluding means (AOM) provided in fluid communication with said pressure chamber; said AOM located between said first opening and a second opening (outlet) of said pressure chamber; c) a patient mouthpiece or Face Mask, in fluid communication with said second opening (outlet); and, d) means for controlling AOM, adapted to interrupt and release said airflow at a predetermined frequency and pressure, thereby applying said FPPs to the mouth cavity of a patient according to a predetermined protocol during operation.

11 Claims, 32 Drawing Sheets

PROTOCOL AND METHODS FOR PULSATING DRUG DELIVERY

This application is the U.S. national phase of International Application No. PCT/IL2009/000961 filed 11 Oct. 2009 which designates the U.S. and claims priority to U.S. Provisional Application No. 61/109,218 filed 29 Oct. 2008, the entire contents of which are hereby incorporated by reference.

FIELD OF THE INVENTION

The present invention generally relates to a pulsating inhaler, and to a method of treating the respiratory disorders.

BACKGROUND OF THE INVENTION

Asthma and COPD (chronic obstructive pulmonary disease) are chronic illnesses requiring lifetime therapy and affect 44 million Americans. The mainstay of treatment is inhaler therapies. The delivery of medications via inhaler is problematic causing decreased efficacy and poor patient compliance. Therefore there is a constant search for improving the delivery of drugs through inhalers and positive pressure pulmonary ventilation.

A problem with current inhalers is that they tend to deposit the medication in the oral cavity, not in the lungs where it is effective. Also, it is difficult to coordinate the delivery of the drug with the expiratory cycle. Because of these problems the accurate dosage of medication cannot be delivered and the treatment causes many side effects. In addition the current inhaler techniques are passive techniques that are based on the ability of the patient to suck the drug into the lungs. As their action on the patient is solely and totally drug-dependent, the above-mentioned faults cause a major problem to the user.

It should be emphasized that positive pressure ventilation devices provide respiratory support of the patient without significant change in the patient's lung function. Furthermore, the aforesaid devices do not have a prolonged influence on the patient's condition after treatment completion.

US Patent Application 20080156319 ('319) to Avni discloses a pulsating inhaler comprising a fluid oscillator providing a focused fluid column with a series of alternating high and low pressures zones, a drug dispenser adapted for releasing small and constant measures of at least one drug via the fluid column, and, at least one outlet orifice adapted to direct the focused fluid column towards the respiratory tract of a patient. The small and constant measures of the drug are delivered to the patient's lungs while its respiratory tracts are gently and continuously vibrated. As acknowledged, applying a sequence of pneumatic pulses to the patient's airways through the oral cavity results in therapeutic effects.

However, '319 does not teach protocols comprising optimal parameters efficacious in treating disorders or for uptake of medicaments.

Providing means and methods of generating and delivering discrete wave trains of different repetition frequencies and pulse amplitudes which are efficacious in treating pulmonary and breathing disorders would fulfill a long felt and unmet need.

Providing means and methods of generating and delivering discrete wave trains of different repetition frequencies and pulse amplitudes which increase the uptake of medications would likewise fulfill a long felt and unmet need.

SUMMARY OF THE INVENTION

It is hence one object of the invention to disclose an air delivery device (ADD) for applying fluid pressure pulses (FPP) to the mouth cavity of a patient at a predetermined frequency according to a protocol of TABLE 1. Table 1 summarizes exemplary protocols disclosed in the present invention.

Another object of the invention is to disclose the ADD comprising (a) an air blower for blowing air into a pressure chamber via a first opening (inlet); (b) an airflow occluding means (AOM) provided in fluid communication with the pressure chamber. The AOM located between the first opening and a second opening (outlet) of the pressure chamber; (c) a patient mouthpiece, in fluid communication with the second opening (outlet); and, (d) means for controlling AOM, adapted to interrupt and release the airflow at a predetermined frequency and pressure, thereby applying said FPPs to the mouth cavity of a patient according to a predetermined protocol during operation.

A further object of the invention is to disclose the pressure chamber additionally provided with a gaseous fluid vibrating means (GFVM), adapted to vibrate the gaseous fluid in the chamber at predetermined frequencies, thereby providing vibrationally modulated FPPs to the mouth cavity of the patient.

A further object of the invention is to disclose the pressure of said FPP greater than ambient gaseous fluid pressure.

A further object of the invention is to disclose the pressure of said FPP less than ambient gaseous fluid pressure.

A further object of the invention is to disclose the ADD provided useful for treating a condition selected from a group consisting of asthma, COPD and CF.

A further object of the invention is to disclose the protocol selected from a group comprising asthma protocol, COPD protocol and CF protocol.

A further object of the invention is to disclose the gaseous fluid as one or a mixture of two or more fluids selected from a group of pharmaceutically acceptable materials consisting of air, oxygen, nitrogen, nitrous-oxide, carbon dioxide, noble gases, medicament-enriched fluid or fluids, anesthetic-enriched fluid or fluids, particles (e.g., salt crystals), fine particles, nano-particles, fillers, flowing matter, ice-crystals liposomes, vesicles, thickifiers, thickeners, mucus viscosity decreasing agents, mucus viscosity increasing agents, fine particles from any plant or microorganism source; genetically modified DNA, biological vectors containing genetically modified DNA, antibodies, proteins, peptides, enzymes, hormones, factors, co-factors, carbohydrates, glycoprotein's, lipoproteins, water-immiscible materials.

A further object of the invention is to disclose the ADD comprises gas heating or cooling means.

A further object of the invention is to disclose the ADD comprises gas humidifying or dehumidifying means.

A further object of the invention is to disclose the ADD comprises means for humidifying said gas with a medicated solution.

A further object of the invention is to disclose the ADD comprises focusing means for the gas flow, especially Venturi-type concentrators and fluid flow facilitators.

A further object of the invention is to disclose the ADD comprises air flow controlling means selected from a group consisting of turbulence inducing means, buffering means and laminar air flow inducing means.

A further object of the invention is to disclose the ADD comprises means of providing the FPPs directly to the lungs or bronchi via a laryngoscope or nasal-cannula.

A further object of the invention is to disclose the ADD comprising means for measuring respiratory parameters and analyzing means.

A further object of the invention is to disclose the respiratory parameters selected form the group consisting of Forced Vital Capacity, Forced Expiratory Volume in 1 Second, Peak Expiratory Flow, Forced Expiratory Flow 25-75% or 25-50%, Forced Inspiratory Flow 25%-75% or 25%-50%, Forced Expiratory Time, Slow Vital capacity, Tidal Volume, Maximum Voluntary Ventilation.

A further object of the invention is to disclose the ADD adapted to analyze variation of the respiratory parameters and optimize the applied therapeutic protocol.

A further object of the invention is to disclose the measuring means comprising at least one sensor adapted to generate an electrical signal corresponding to a detected airflow in the patient's airways.

A further object of the invention is to disclose the sensor that is at least one transducer adapted to detect an acoustic wave and to transmit a corresponding electrical signal to the analyzing means.

A further object of the invention is to disclose the analyzing means is adapted to vary optimize said therapeutic protocol according to detected respiratory parameters.

A further object of the invention is to disclose the ADD further comprising means for measuring characteristics of the FPPs and means for adjusting the characteristics according to predetermined protocol.

A further object of the invention is to disclose the characteristics chosen from the group consisting of frequency and pressure amplitude of FPP.

A further object of the invention is to disclose the adjusting means controlled automatically.

A further object of the invention is to disclose the adjusting means controlled manually.

A further object of the invention is to disclose the pressure chamber fed with compressed air from an outer compressed-air source.

A further object of the invention is to disclose the ADD adapted for continuous positive airway pressure (CPAP) therapy.

A further object of the invention is to disclose the ADD integrated with a CPAP device.

A further object of the invention is to disclose the ADD integrated with CPAP device.

A further object of the invention is to disclose the ADD integrated with a respiratory pipe.

A further object of the invention is to disclose the ADD integrated with a mouthpiece.

A further object of the invention is to disclose a method for treating mammals, comprising steps of (a) applying fluid pressure impulses (FPP) at a predetermined frequency according to a protocol as defined in TABLE 1; and (b) applying the same to the mouth cavity of a patient.

A further object of the invention is to disclose the method comprising steps of (a) obtaining an ADD; the ADD comprises an air blower for blowing air into a pressure chamber via a first opening (inlet); an airflow occluding means (AOM) provided in fluid communication with said pressure chamber; the AOM located between said first opening and a second opening (outlet) of the pressure chamber or between the blower and the outlet in case of the hand held drug inhaler; a patient mouthpiece, in fluid communication with the second opening (outlet); and, means for controlling AOM, adapted to interrupt and release said airflow at a predetermined frequency and pressure, thereby applying said FPPs to the mouth cavity of a patient according to a predetermined protocol during operation; (b) fitting the mouthpiece or face mask to the patient's air cavity; (c) selecting a predetermined protocol with (d) controlling means; and, (e) operating the protocol; such that FPPs are administered to the mouth cavity of the patient according to the predetermined protocol.

A further object of the invention is to disclose the method comprising steps of (a) providing said pressure chamber with an air vibrating means (AVM) for vibrating air in the chamber at predetermined frequencies and (b) operating said AVM, thereby providing vibrating FPPs to the mouth cavity of said patient.

A further object of the invention is to disclose the method additionally comprising steps of providing said FPPs at greater than ambient air pressure.

A further object of the invention is to disclose the method additionally-comprising steps of providing said FPP at lower than ambient air pressure.

A further object of the invention is to disclose the method additionally comprising steps of providing an ADD device useful in treating a condition selected from a group comprising asthma, COPD and CF.

A further object of the invention is to disclose the method additionally comprising steps of (a) producing FPPs at a predetermined frequency according to a predetermined protocol.

It is a core purpose of the invention to provide the method additionally comprising steps of (a) selecting the protocol from a group comprising asthma protocols, COPD protocols and CF protocols and (b) administering the same to the mouth cavity of a patient.

It is a core purpose of the invention to provide means and methods of accurately measuring the frequency characteristics of the FPPs. It is a further purpose of the invention to provide means and methods of relaying the aforementioned data to the microprocessor of the device, and to process the data, such that the operation of the device can be adjusted or calibrated or attenuated by the patient or doctor. Similarly, it is a core purpose of the invention to provide means and methods or accurately measuring the pressure amplitude of the FPPs. It is a further purpose of the invention to provide means and methods of relaying the aforementioned data to the microprocessor of the device, and to process the data, such that the operation of the device can be adjusted or calibrated or attenuated by the patient or doctor. It is a core purpose of the invention to provide means and methods of controlling pressure variations positively or negatively in order to improve treatment by means of the FPPs. It is a further purpose of the invention to provide means and methods of relaying the aforementioned data to the microprocessor of the device, and to process the data, such that the operation of the device can be adjusted or calibrated or attenuated by the patient or doctor.

It is a core purpose of the invention to provide means and methods of controlling air flow direction positively or negatively in order to improve treatment by means of the FPPs. It is a further purpose of the invention to provide means and methods of relaying the aforementioned data to the microprocessor of the device, and to process the data, such that the operation of the device can be adjusted or calibrated or attenuated by the patient or doctor. The airflow direction can oppose the expirations or inspirations of the patient or be in the same direction, all according to a specific protocol.

A further object of the invention is to disclose a protocol for applying the FPP by the ADD. The aforesaid protocol comprises (a) obtaining an ADD and (b) applying the FPP to the mouth cavity of a patient at frequencies, pressures and intervals according to TABLE 1.

A further object of the invention is to disclose a protocol for applying said FPP by the ADD comprising obtaining said ADD. The ADD comprises (a) an air blower for blowing air into a pressure chamber via a first opening (inlet); (b) an airflow occluding means (AOM) provided in fluid communication with the pressure chamber; the AOM located between said first opening and a second opening (outlet) of the pressure chamber; (b) a patient mouthpiece or a face mask, in fluid communication with the second opening (outlet); (c) means for controlling AOM, (d) operating said ADD, and (e) applying the FPP to the mouth cavity of a patient at frequencies, pressures and intervals according to TABLE 1.

A further object of the invention is to disclose the method further comprising the step of measuring characteristics of the FPPs adjusting the characteristics according to predetermined protocol.

A further object of the invention is to disclose the step of measuring the characteristic comprises at least one element of the group consisting of frequency measuring and pressure amplitude measuring.

A further object of the invention is to disclose the step of adjusting the characteristic is performed automatically.

A further object of the invention is to disclose the step of adjusting the characteristic is performed manually.

BRIEF DESCRIPTION OF THE DRAWINGS

In order to understand the invention and to see how it may be implemented in practice, a plurality of embodiments is adapted to now be described, by way of non-limiting example only, with reference to the accompanying drawings, in which

FIGS. 12A-12I are schematic cross-sectional views of the air delivery device fed with air from the compressed-air line.

DETAILED DESCRIPTION OF THE INVENTION

Figure 1:
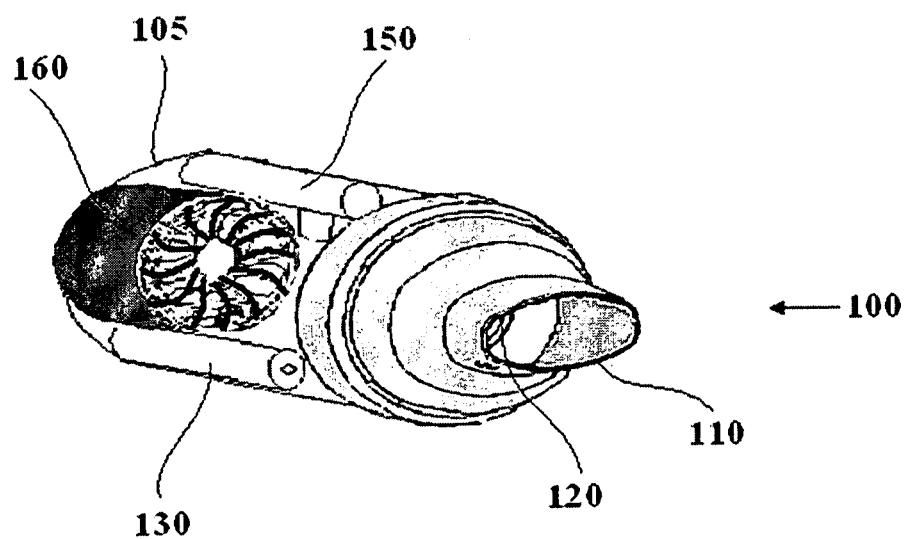
FIG. 1 is a schematic view of the air delivery device.

The following description is provided, alongside all chapters of the present invention, so as to enable any person skilled in the art to make use of said invention and sets forth the best modes contemplated by the inventor of carrying out this invention. Various modifications, however, are adapted to remain apparent to those skilled in the art, since the generic principles of the present invention have been defined specifically to provide an air delivery device and method of using the same.

The term 'Asthma' hereinafter refers to a chronic condition involving the respiratory system in which the airways occasionally constrict, become inflamed, and are lined with excessive amounts of mucus, often in response to one or more triggers. These episodes may be triggered by such things as exposure to an environmental stimulant such as an allergen, environmental tobacco smoke, cold or warm air, perfume, pet dander, moist air, exercise or exertion, or emotional stress. In children, the most common triggers are viral illnesses such as those that cause the common cold. This airway narrowing causes symptoms such as wheezing, shortness of breath, chest tightness, and coughing. The airway constriction responds to bronchodilators. Between episodes, most patients feel well but can have mild symptoms and they may remain short of breath after exercise for longer periods of time than the unaffected individual. The symptoms of asthma, which can range from mild to life threatening, can usually be controlled with a combination of drugs and environmental changes.

The term 'chronic obstructive pulmonary disease (COPD)' hereinafter refers to a disease of the lungs in which the airways become narrowed. This leads to a limitation of the flow of air to and from the lungs causing shortness of breath. In contrast to asthma, the limitation of airflow is poorly reversible and usually gradually gets worse over time. COPD is caused by noxious particles or gases, most commonly from smoking, which triggers an abnormal inflammatory response in the lung. The inflammatory response in the larger airways is known as chronic bronchitis, which is diagnosed clinically when people regularly cough up sputum. In the alveoli, the inflammatory response causes destruction of the tissue of the lung, a process known as emphysema. The natural course of COPD is characterized by occasional sudden worsening of symptoms called acute exacerbations, most of which are caused by infections or air pollution.

The term 'cystic fibrosis' (CF) or mucoviscoidosis, or mucoviscidosis) hereinafter refers to a hereditary disease that affects the exocrine (mucus) glands of the lungs, liver, pancreas, and intestines, causing progressive disability due to multisystem failure. Thick mucus production, as well as a less competent immune system, results in frequent lung infections. Diminished secretion of pancreatic enzymes is the main cause of poor growth, fatty diarrhea and deficiency in fat-soluble vitamins. Males can be infertile due to the condition of congenital bilateral absence of the vas deferens. Often, symptoms of CF appear in infancy and childhood. Meconium ileus is a typical finding in newborn babies with CF. Individuals with cystic fibrosis can be diagnosed prior to birth by genetic testing. Newborn screening tests are increasingly common and effective (although false positives may occur, and children need to be brought in for a sweat test to distinguish disease vs carrier status). The diagnosis of CF may be confirmed if high levels of salt are found during a sweat test, although some false positives may occur. There is no cure for CF, and most individuals with cystic fibrosis die young: many in their 20s and 30s from lung failure. However, with the continuous introduction of many new treatments, the life expectancy of a person with CF is increasing to ages as high as 40 or 50. Lung transplantation is often necessary as CF worsens. Cystic fibrosis is one of the most common life-shortening, childhood-onset inherited diseases. In the United States, 1 in 3,900 children is born with CF. It is most common among Europeans and Ashkenazi Jews; one in twenty-two people of European descent are carriers of one gene for CF, making it the most common genetic disease in these populations: Ireland has the highest rate of CF carriers in the world (1 in 19). CF is caused by a mutation in a gene called the cystic fibrosis transmembrane conductance regulator (CFTR). The product of this gene is a chloride ion channel important in creating sweat, digestive juices, and mucus. Although most people without CF have two working copies (alleles) of the CFTR gene, only one is needed to prevent cystic fibrosis. CF develops when neither allele can produce a functional CFTR protein. Therefore, CF is considered an autosomal recessive disease.

The term 'spirometry' (meaning the measuring of breath) hereinafter refers to the most common of the Pulmonary Function Tests (PFTs), measuring lung function, specifically the measurement of the amount (volume) and/or speed (flow) of air that can be inhaled and exhaled. Spirometry is an important tool used for generating pneumotachograph to assessing conditions such as asthma, pulmonary fibrosis, CF, and COPD. The spirometry test is performed using a device called a spirometer, which comes in several different varieties. Most spirometers display the following graphs: (a) a volume-time curve, showing volume (liters) along the Y-axis and time (seconds) along the X-axis; and (b) a flow-volume loop, which graphically depicts the rate of airflow on the Y-axis and the total volume inspired or expired on the X-axis.

The term 'aspirator', also called an eductor-jet pump or filter pump, hereinafter refers to a device that produces vacuum by means of the Venturi effect. In the aspirator, fluid (liquid or gaseous) flows through a tube which then narrows. When the tube narrows, the fluid's speed increases, and because of the Venturi effect, its pressure decreases. Vacuum is taken from this point.

The term 'positive airway pressure' (PAP) hereinafter refers to a method of respiratory ventilation used primarily in the treatment of sleep apnea, for which it was first developed. PAP ventilation is also commonly used for critically ill patients in hospital with respiratory failure, and in newborn infants (neonates). In these patients, PAP ventilation can prevent the need for endotracheal intubation, or allow earlier extubation. Sometimes patients with neuromuscular diseases use this variety of ventilation as well.

For purposes of the current invention, the term 'therapeutic protocol' hereinafter refers to a description of the therapeutic procedure unlimitedly defining frequency and amplitude of the provided FPPs, treatment period, and medicines optionally inserted into the air flow.

Core Features of the Invention

It is a core object of the invention to provide means and methods for applying fluid pressure pulses (FPP) to the mouth cavity of a patient at a predetermined frequency according to a protocol of TABLE 1.

The following three core features of the invention clearly and emphatically distinguish it from prior art:

Firstly, the fluid pressure pulses (FPPs) provided by the present invention are in fact discrete pressurised air packets produced by a shutter action which "chops" and interupts the air stream. In the embodiments of the present invention this is done by airflow occluding means (AOM) as described and illustrated herein. In the prior art, pulses of a very different type are produced, usually by pistons or impellors: in these cases blasts or gusts of air are produced by the impellers and thrown forward; the variation of pressure between such blasts is less abrupt, and more wave like.

Secondly, the present invention supplies fluid pressure pulses (FPP) to the mouth cavity of a patient at a predetermined frequency and pressure in a predetermined manner which is not dependent upon the natural breathing rate of the patient. The patient breathes normally, whilst receiving the FPPs on inspiration and expiration. During inspiration the supplied FPPs are in the same direction as the air being breathed in, and during expiration the FPPs meet resistance of the air being breathed out. Both circumstances have a therapeutic effect.

A third important core feature of the present invention are the tailor made protocols for the diseases herein disclosed, especially asthma, COPD, CF Reference is now made to FIG. 1, presenting an air delivering device 100 adapted for applying fluid pressure pulses (FPP) to the mouth cavity of a patient according to, a predetermined protocol. The aforesaid device 100 comprises a housing 105 accommodating a battery 130, a blower 160, a drug container 150, and an inhalation/exhalation valve 120. The blower energized by the battery 130 pumps air into the housing 105. The air is exhausted from the mouthpiece 110 or any kind of a respiratory mask through the valve 120. Thus, the device 100 when in fluid contact with a human oral cavity provides air pressure stimulating the intensification of gas exchange in the human lungs.

Figure 2A:
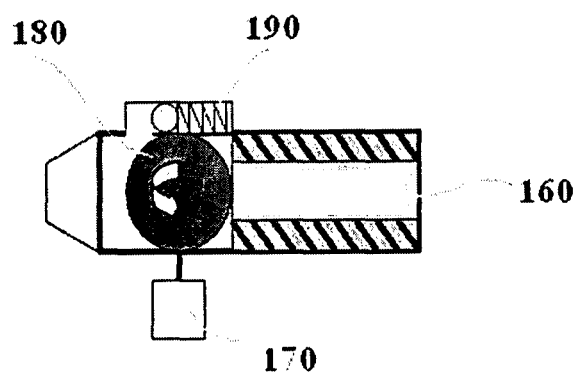
FIGS. 2A-2C are schematic views of the air delivery device provided with the rotary choke modulator.
Figure 2B:
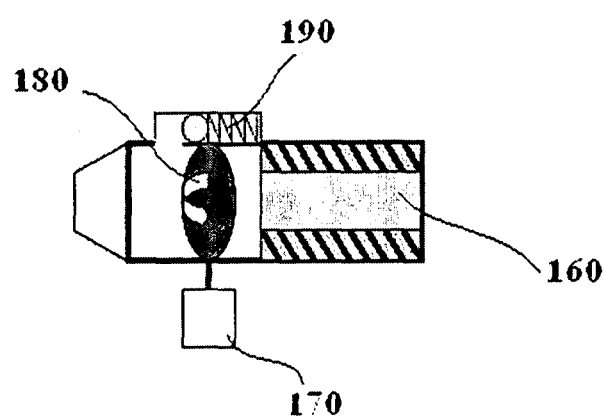
Figure 2C:
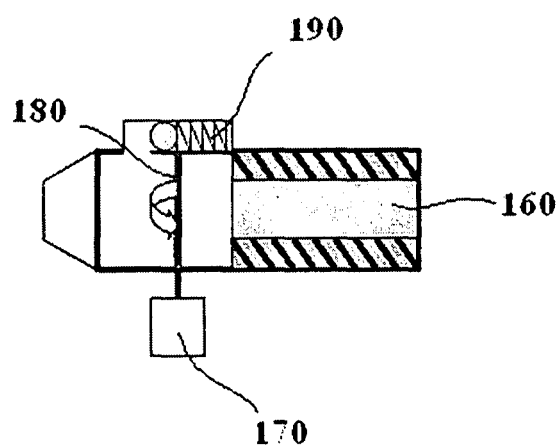

Reference is now made to FIGS. 2a-2c, showing an embodiment of the current invention provided with a rotating choke 180. The blower 160 creates air flow in which air pressure is modulated by means of the aforesaid rotating choke 180. The excess pressure is exhausted through a valve 190. FIGS. 2a-2c present different positions of the rotating choke. The choke rotation provides modulation of the pressure delivered to the human oral cavity for intensification of gas exchange in the human lungs.

Figure 3A:
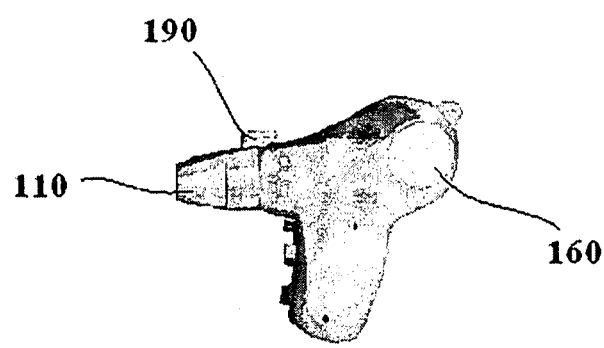
FIGS. 3A-3B are external views of the pocket air delivery device.
Figure 3B:
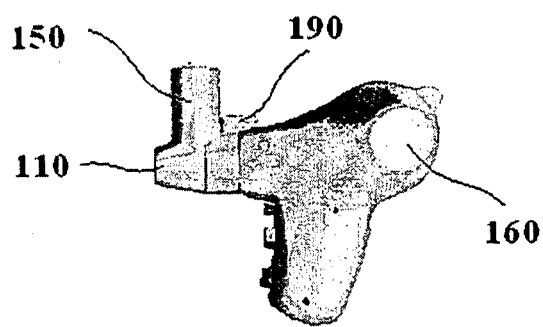

Reference is now made to FIG. 3a-3b, presenting external views of two embodiments provided with the drug container 150 (FIG. 3b) and without it (FIG. 3a). The air flow exhausted from the mouthpiece 110 is optionally comprises a drug for inhaling into the human lungs. The aforesaid drug is dispensed into the air flow from the dug container 150.

Figure 4A:
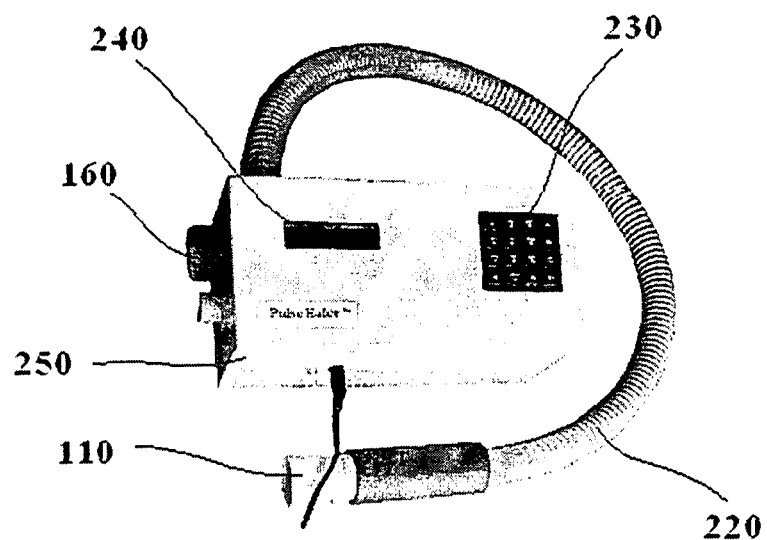
FIG. 4A is an external view of the air delivery device provided with the respiratory hose.
Figure 4B:
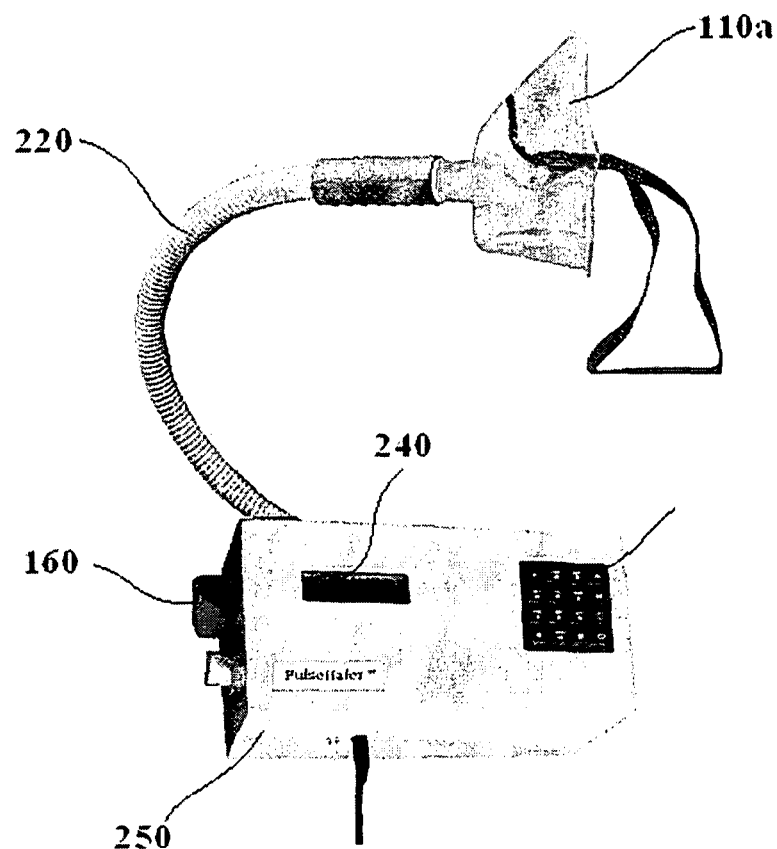
FIG. 4B is an external view of the air delivery device provided with the hose connected to the respiratory mask.
Figure 4C:
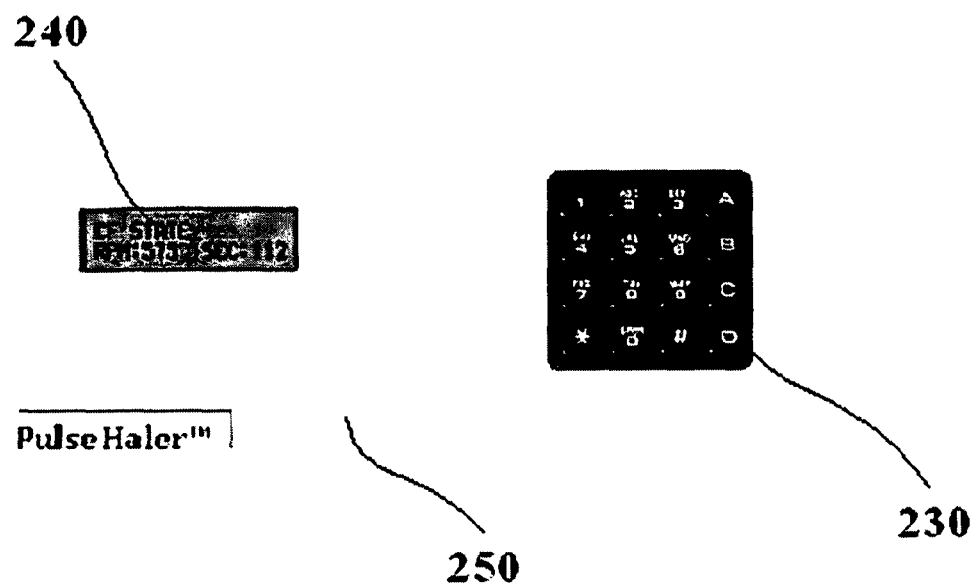
FIG. 4C is an external view of the control unit of the air delivery device.

Reference is now made to FIGS. 4a-4c, showing the air delivery device provided with a respiratory hose 220 and mouthpiece 110 or a respiratory mask 110a. The main body 250 comprises the blower 160, a keypad 230, and a display 240. A patient or a doctor can program the aforesaid device to provide the air flow with a predetermined pressure protocol. The aforesaid device is preprogrammed for a number of therapeutic protocols adapted for treatment of airway diseases such as asthma, COPD and CF. Other diseases of airway are in the scope of the current invention, as well.

Figure 5:
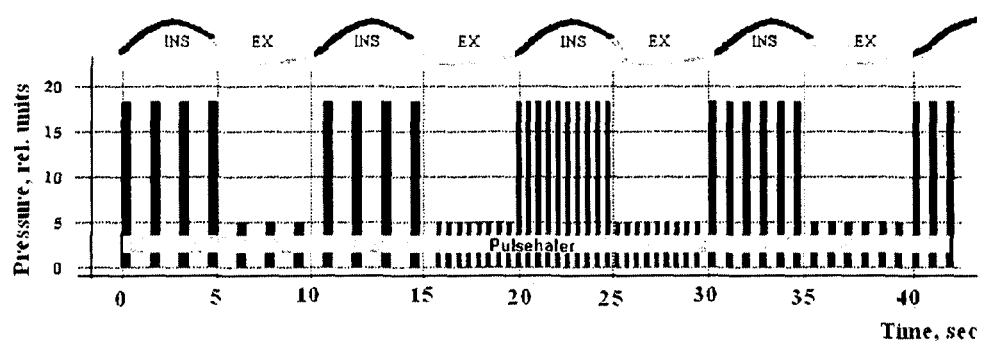
FIG. 5 is a graph of the pressure profile provided by the air delivery device.

Reference is now made to FIG. 5, presenting a graph of a temporal dependence of pressure delivered to the patient's oral cavity. In accordance with proposed technical solution, a delivered pressure profile comprises alternation of pneumatic pulse sequences of high and low amplitudes corresponding to inhalation and exhalation, respectively. Amplitude and repetition rate of the pneumatic pulses are preprogrammed by a patient or a doctor according to the treated disease.

Figure 6:
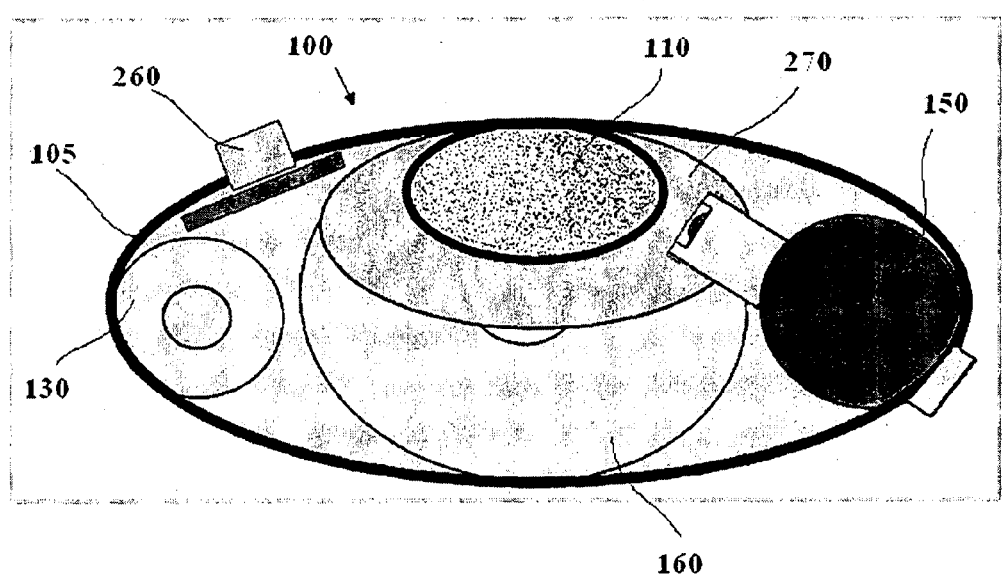
FIG. 6 is a schematic cross-sectional view of the pocket air delivery device.
Figure 7A:
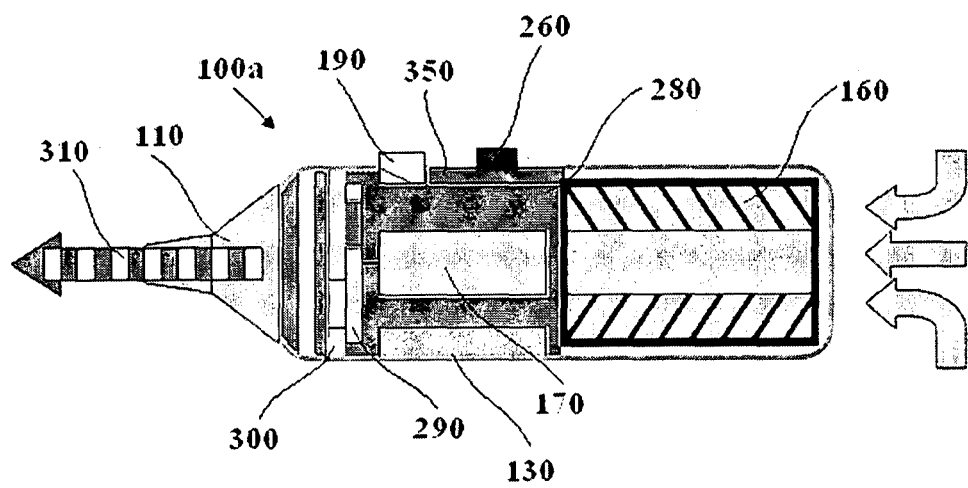
FIGS. 7A-7B are schematic cross-sectional views of the air delivery device provided with the longitudinal rotary disk valve.

Reference is now made to FIG. 6, showing a schematic cross-sectional view of the air delivery device 100. The housing 105 accommodates a battery 130, a drug container 150, and a blower 160 controlled by a switch 260. A drug dose 270 is admixed to air pumped by the blower 160 is delivered into the patient's mouth through a mouthpiece 110 or any kind of a respiratory mask Reference is now made to FIG. 7a, presenting a schematic cross-sectional of an air delivery device 100a provided with a rotary disk valve formed by two discs, specifically, a fixed disc 300 and a rotary disc 290. A blower 160 is energized by a battery 130 and controlled by a switch 260 connected to a controlled unit 350. The aforesaid blower 160 pumps air from surrounding space into a chamber 280. The control unit 350 is preprogrammed for providing pneumatic pulses according to a predetermined protocol. The pneumatic pulses are produced by means of the rotary disc valve. The rotary disc 290 is set into motion by a motor 170. Thus, the device 100a delivers a sequence 310 of pneumatic pulses into the patient's oral cavity (not shown) through a mouthpiece 110. A pressure-relief valve 190 prevents output pressure from exceeding a predetermined value. The excess pressure is exhausted through the aforesaid valve 190. The disc can be described as acting as a shutter, which chops the air stream.

Figure 7B:
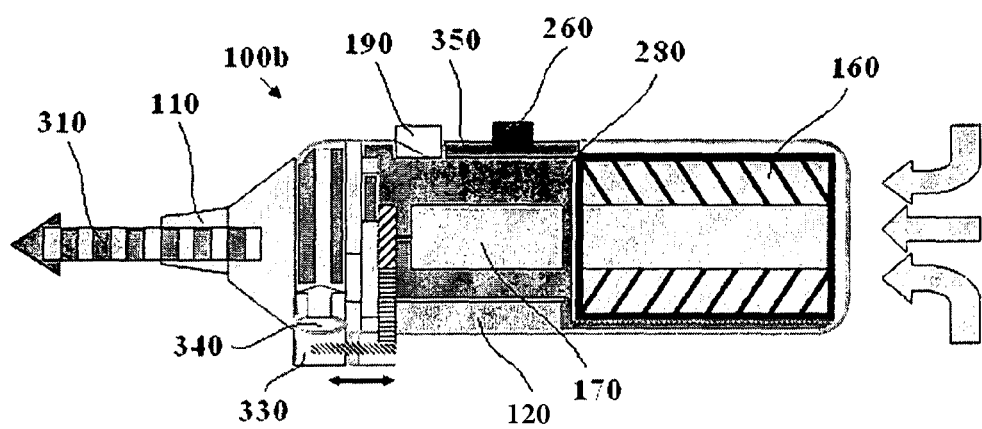

Reference is now made to FIG. 7b, presenting an embodiment of the current invention in which an air delivery device 100b is further provided with a drug container 330 furnished with an one-way valve 340 adapted for dispensing the drug accommodated in the container 330. The aforesaid drug is admixed to the air pumped by the blower 160.

Figure 8A:
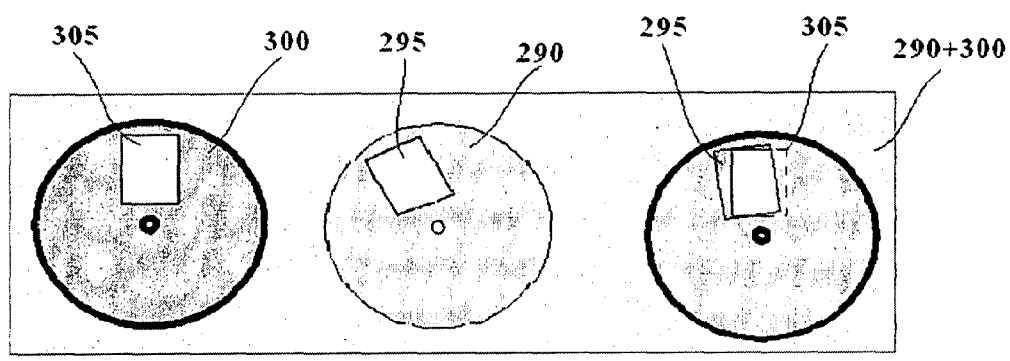
FIGS. 8A-8B are schematic diagrams of the relative disc position in the rotary disk valve.
Figure 8B:
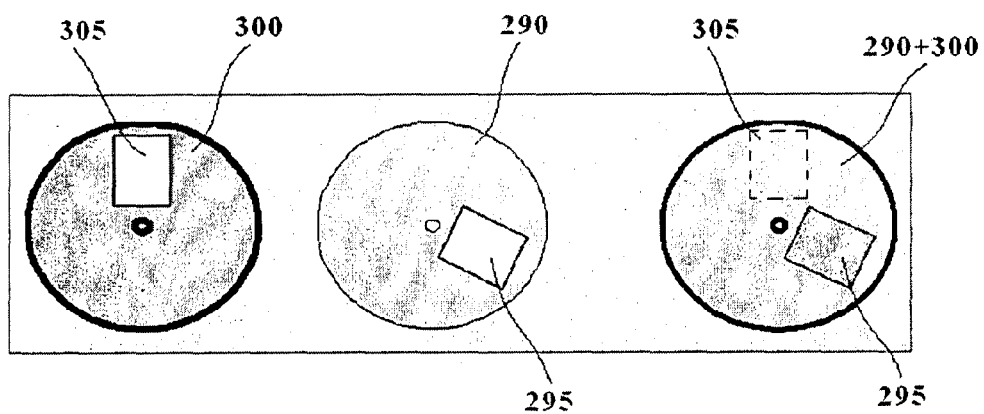

Reference is now made to FIGS. 8a-8b, specifying a working principle of the rotary disc valve. A rotary disc 290 and a fixed disc 300 have openings 295 and 305, respectively. The rotary disc 290 rotates relative to the fixed disc 390. The openings periodically coincide, allowing air to pass though the valve, creating a shutter-like effect. FIGS. 8a and 8b show positions of discs 290 and 300 in the coincident and non-coincident positions, respectively. FIG. 8a presents the disc positions corresponding to an open state of the valve, FIG. 8b to a closed state, somewhat like a camera shutter. Thus, alternating the open and closed states by rotating the disc 290 provides a sequence of pneumatic pulses. Turning frequency (rpm) defines the repetition frequency of the aforesaid pneumatic pulses. The aforementioned turning frequency is known herein as the Avni effect.

Figure 9A:
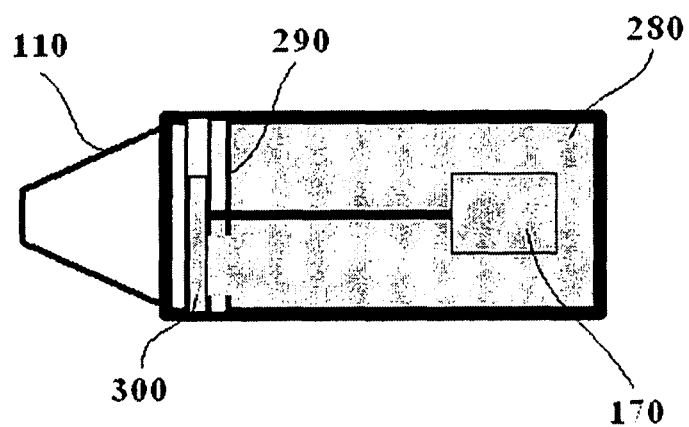
FIGS. 9A-9B are schematic cross-sectional views of the rotary disk valve.
Figure 9B:
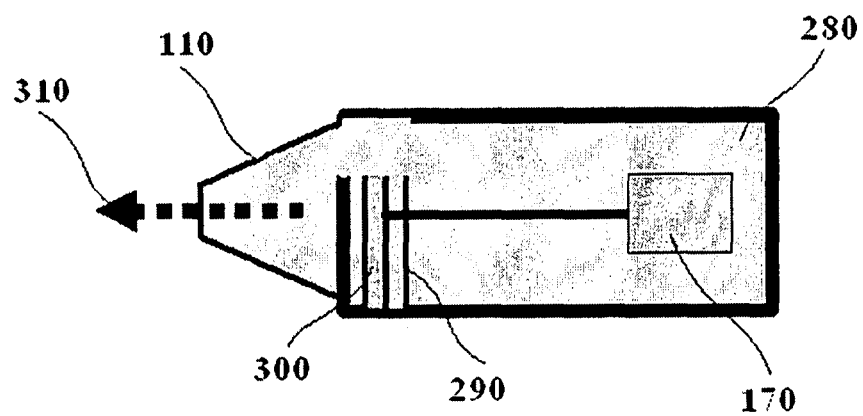

Reference is now made to FIGS. 9a-9b, elucidating an arrangement of the rotary disc valve. As said above, coincident and non-coincident positions correspond to open and closed states of the rotary disc valve. FIG. 9a shows non-coincidence of openings of discs 290 and 300 resulting in the closed state of the valve. FIG. 9b presents the positions of the discs 290 and 300 allowing the air accommodated in the chamber 280 to pass into the mouthpiece 110 because of disc opening coincidence.

Figure 10A:
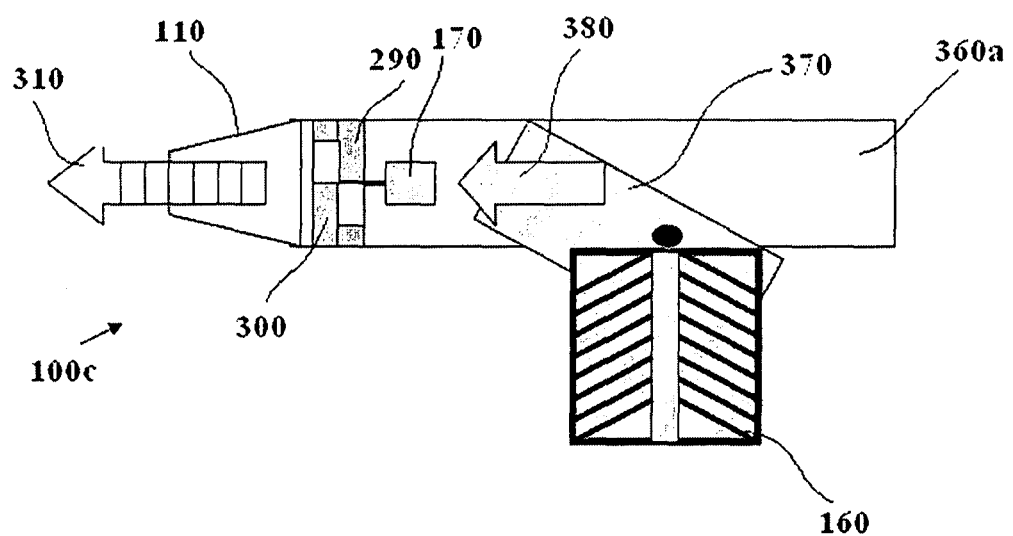
FIGS. 10A-10B are schematic cross-sectional views of the air delivery device provided with the aspirator-based modulator.
Figure 10B:
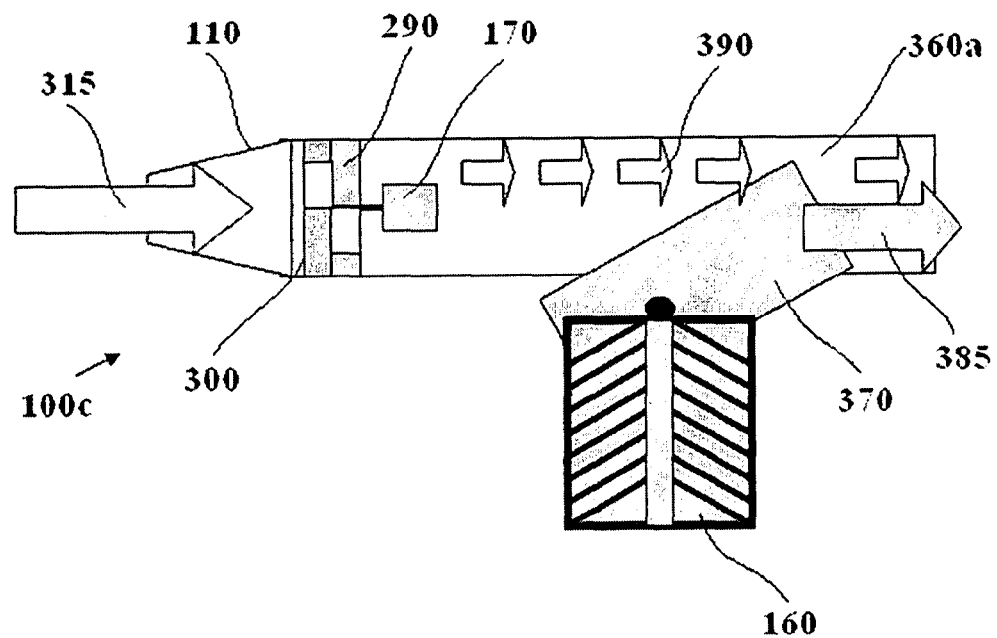

Reference is now made to FIGS. 10a-10b, presenting an embodiment 100c of the air delivering device provided with a redirectable ejector nozzle 370. According to FIG. 10a, the ejector nozzle 370 is directed to the rotary disc valve and dispenses the air provided by the blower 160. The compressed air dispensed from nozzle 370 entrains neighboring air 380 accommodated in open receptacle 360a. The air passes through the rotary disc valve which forms a sequence of the pneumatic pulses. FIG. 10b presents the air delivering device in which the redirectable ejector nozzle 370 is oppositely directed. Air rarefication or decompression is achieved by means of entraining air 385 accommodated in the receptacle 360a by the air dispensed from the ejector nozzle 370. The air is drawn off the human oral cavity through the rotary disc valve. Thus, the air delivering device 100c provides alternated air pressurization/rarefication (or decompression) in the oral cavity resulting in therapeutic effects in the airways of a human being.

Reference is now made to FIGS. 11a-11d, presenting an embodiment 100d of the air delivering device provided with an eccentric pneumatic modulator formed by an eccentric actuator 400 and a membrane 410. The pressure in the air stream from the blower 160 is modulated by the membrane 410 that is moved between positions A and B shown in FIGS. 11a and 11b, respectively. Thus, the pressure of the air provided for inhaling into the human oral cavity is high-frequency-modulated.

Figure 11A:
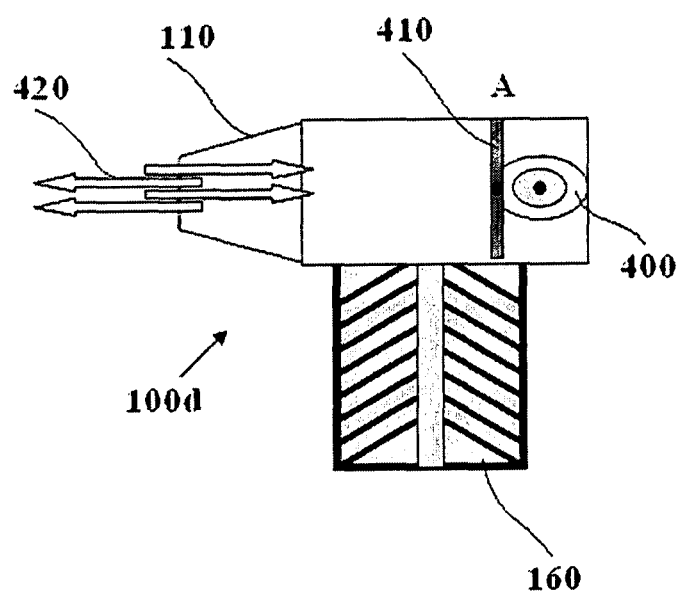
FIGS. 11A-11D are schematic cross-sectional views of the air delivery device provided with the eccentric pneumatic modulator.
Figure 11G:
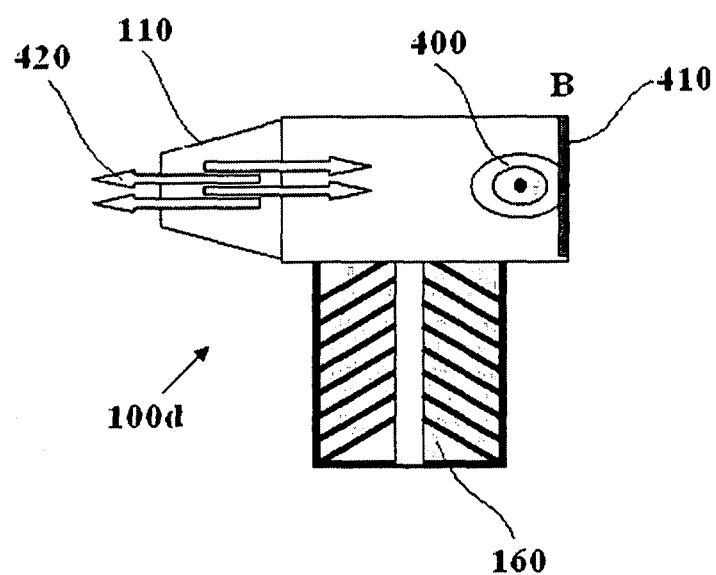
Figure 11C:
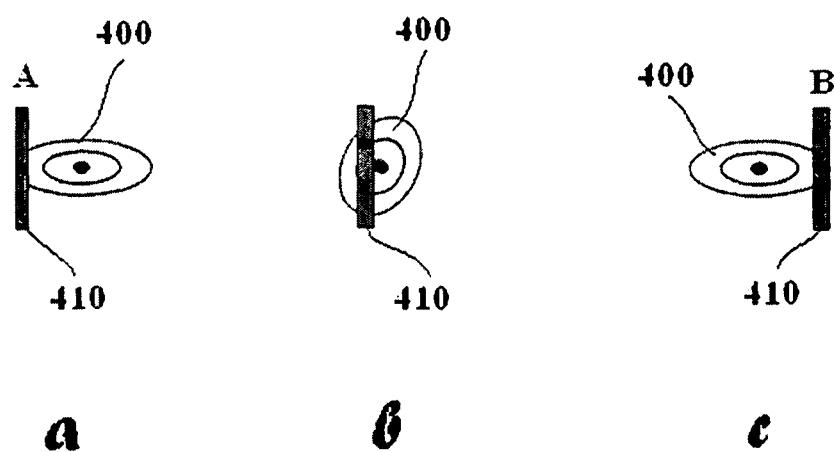

Reference is now made to FIG. 11c, specifying operation of the eccentric pneumatic modulator. The eccentric actuator 400 provides cyclic movement of the membrane 410 resulting in high-frequency modulation of the pressure in air stream. The pivotal eccentric actuator 400 reciprocatively drive the membrane 410.

Figure 11D:
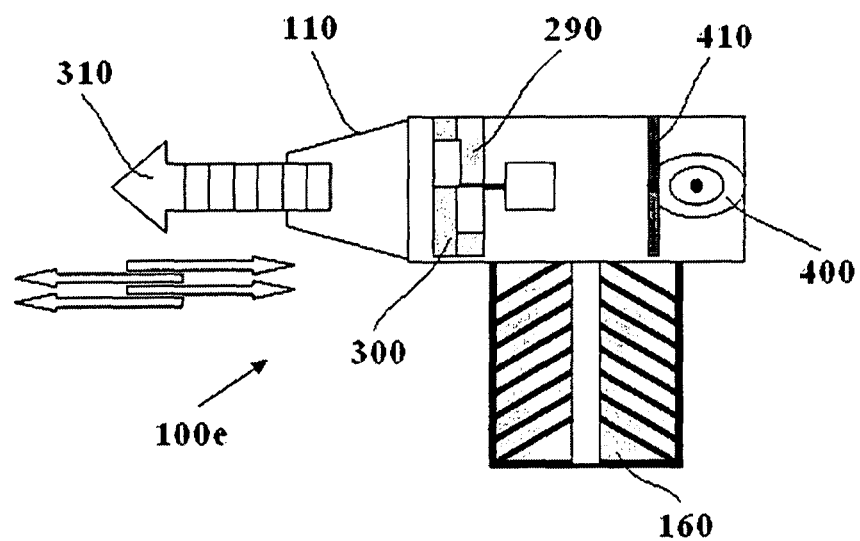

Reference is now made to FIG. 11d, showing an embodiment 100e of the air delivering device provided with two means for modulating the air pressure of the air provided into the patient's oral cavity, specifically, the rotary disc valve and the eccentric pneumatic modulator. The air delivering device 100e is able to concurrently modulate the provided air pressure at two frequencies.

Figure 12A:
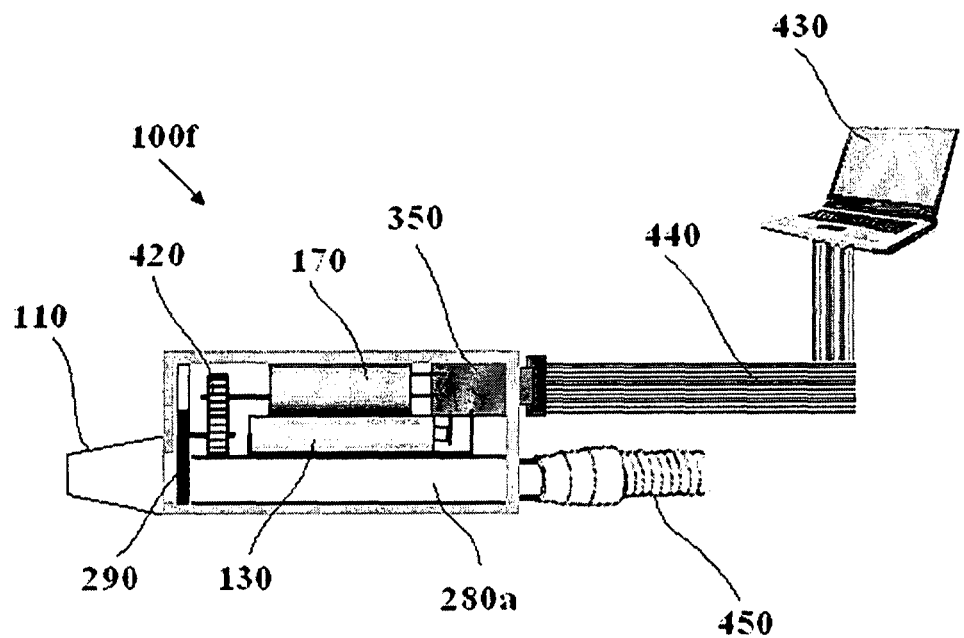
Figure 12G:
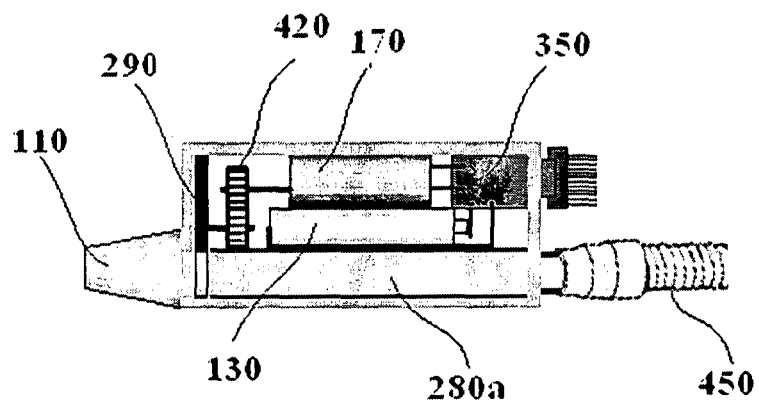
Figure 12C:
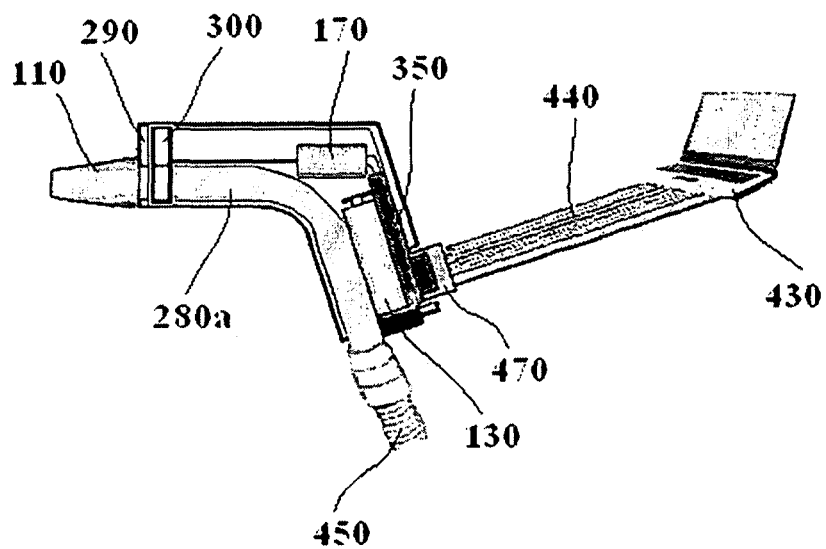
Figure 13A:
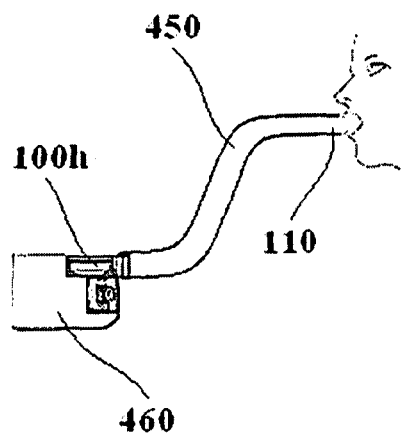
FIGS. 13A-13C are schematic views of the air delivery device combined with CPAP device.
Figure 13B:
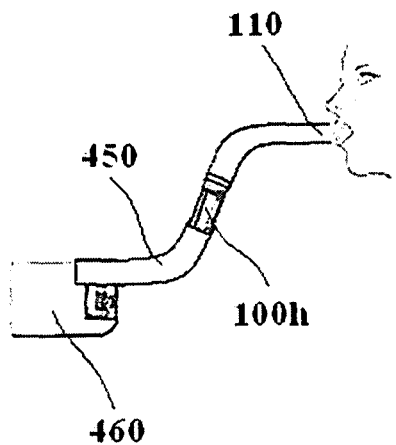

Reference is now made to FIGS. 12a-12c, presenting a specific embodiment 100f of the current invention adapted for providing PAP therapy of sleep apnea patients. The present technical solution comprises an air delivery device fed with air from the compressed-air line 450. The aforesaid device provides FPPs to the patient's oral cavity per a mouth piece 110. A prescribed therapeutic protocol is transmitted to a control unit 350 by a personal computer 430 through a communication line 440 and a connector 470. The control unit 350 controls an electrical motor 170 energized by a battery 130. A disc 290 is driven by the electrical motor 170 mechanically connected to the disc 290 through a gear 420. The rotating disc 290 periodically opens and closes a chamber 280a filled with compressed air fed a central line 450 providing FPPs according to a predetermined protocol. FIGS. 13a and 13b present air delivery device in closed and open states, respectively.

Figure 12D:
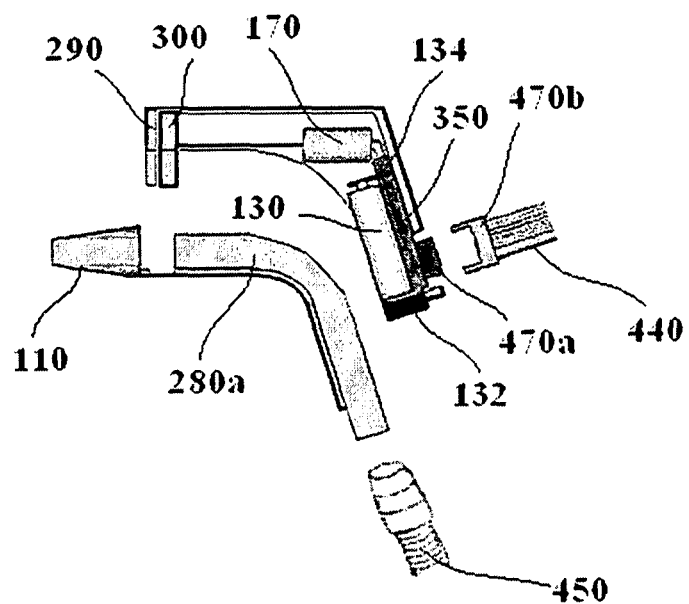
Figure 12E:
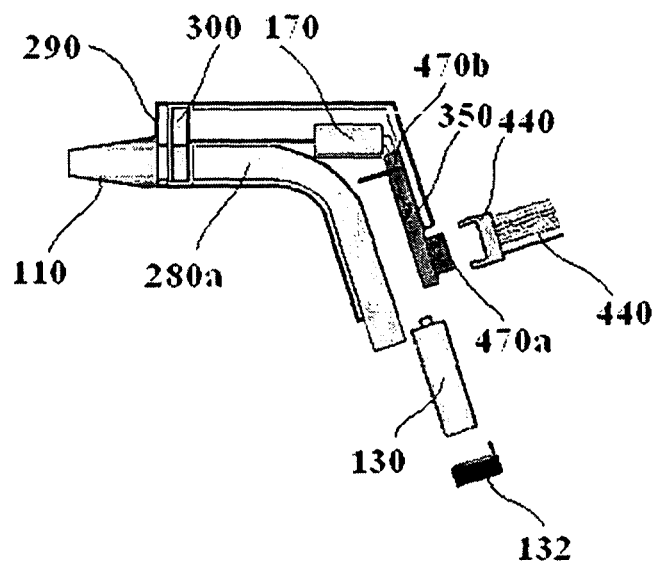

Reference is now made to FIGS. 12d and 12e, presenting partially exploded views of the aforesaid embodiment 100f. Specifically, male and female portions 470a and 470b are indicated. Further, battery contacts 132 and 134 are designed for tapping off the battery voltage.

Figure 12F:
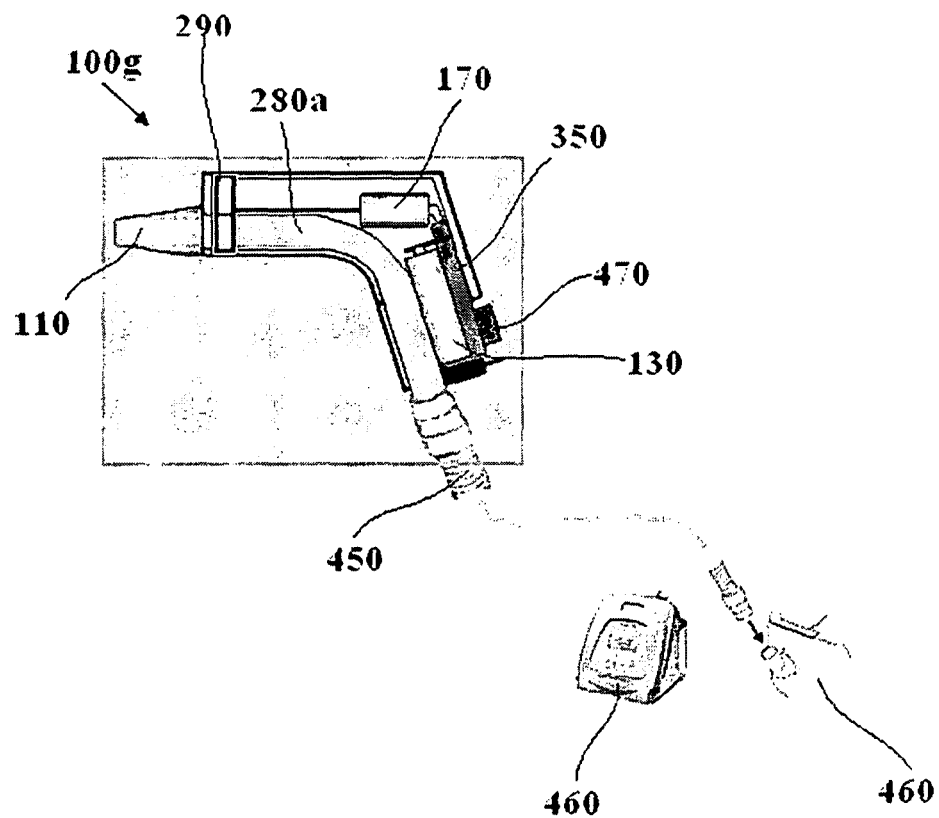
Figure 12G:
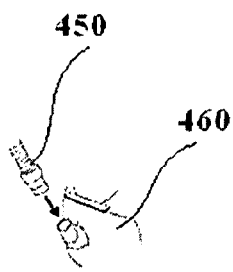

Reference is now made to FIG. 12f, showing the embodiment 100g, of the current invention that is connected to a CPAP device 460 and is fed with pressurized air from it. The aforesaid embodiment 100g is applicable for home use.

Figure 12H:
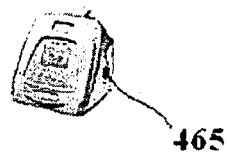
Figure 12I:

Reference is now made to FIGS. 12g-12i, presenting a connection configuration of the air pipe 450 and the CPAP device 460. Optionally, the device 460 is adapted to humidify the provided pressurized air. A control button is indicated with numeral 465. Different models of aforesaid CPAP devices are presented in FIG. 12i.

The proposed device is adapted for pneumatic therapy of sleep apnea patient. The aforesaid device can be use as OEM device in mass production of CPAP therapeutic devices.

Figure 13C:
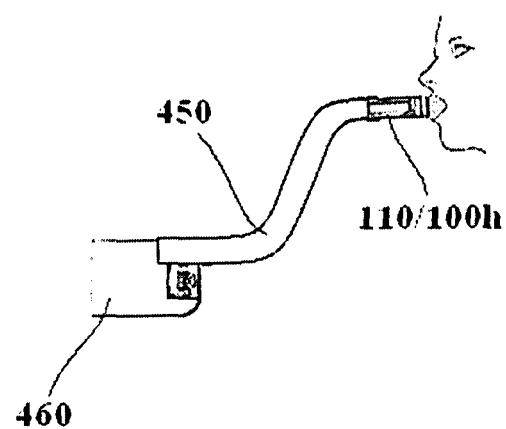

Reference is now made to FIGS. 13a-13c, presenting alternative exemplary embodiments of the air deliver device in a combination with CPAP device 460. As shown in FIG. 13a, the device 100h is integrated with the CPAP device (the ADD is at least partially within the housing of the CPAP itself). In accordance with another embodiment of the current invention, the device 100h is disposed into the air pipe 450. Integration of the device 100h into the mouthpiece 110 is also well within the scope of the current invention. It is herein acknowledged that sufficient description is disclosed so that other combinations of the ADD with a CPAP device which will occur to a person skilled in the art are in fact enabled here, and are well within the scope of the present invention. It is further acknowledged that the above ADD may be combined with CPAP equipment as Original Equipment Manufacture (OEM) or after sales. It is yet further acknowledged that such combinations may be reversible. In other words, the ADD may be clipped, slotted or otherwise integrated or embedded within any part of a CPAP system or device.

Reference is now made to a core purpose of the invention to provide means and methods of accurately measuring the frequency characteristics of the FPPs. It is a further purpose of the invention to provide means and methods of relaying the aforementioned data to the microprocessor of the device, and to process the data, such that the operation of the device can be adjusted or calibrated or attenuated by the patient or doctor. Similarly, it is a core purpose of the invention to provide means and methods of accurately measuring the pressure amplitude of the FPPs. It is a further purpose of the invention to provide means and methods of relaying the aforementioned data to the microprocessor of the device, and to process the data, such that the operation of the device can be adjusted or calibrated or attenuated by the patient or doctor. It is a core purpose of the invention to provide means and methods of controlling pressure variations positively or negatively in order to improve treatment by means of the FPPs. It is a further purpose of the invention to provide means and methods of relaying the aforementioned data to the microprocessor of the device, and to process the data, such that the operation of the device can be adjusted or calibrated or attenuated by the patient or doctor.

Example

Medical test trial performed by Dr. Gershon Fink, Head of the Israel society of pulmonology, Head of the Pulmonary Institute, Kaplan Medical Center.

The treatment was performed by to delivering series of air packets (discrete wavetrains of different repetition frequencies and pulse amplitudes) according to predetermined protocols in Table 1. The frequencies are electronically controlled. This ensures accurate frequency and pressure delivery of each air packet. The air packets are delivered for a pre-specified time period.

Without wishing to be bound by theory discrete wavetrains of different repetition frequencies and pulse amplitudes result in specific therapeutic effects on the various components of the lung tissue, e.g. Bronchial smooth muscles and blood vessels relaxation, mucus clearance of the airways, reduction of the pulmonary vascular pressure etc.

The immediate effects of the air delivering device were studied on seven patients suffering from Chronic Bronchitis.

A baseline Pulmonary Function test (PFT) was performed prior to the start of the trial.

The PFT were abnormal in six of seven patients.

All the patients had baseline shortness of breath, difficult breathing and difficult mucus clearance.

Each person used the device for one session of 18 minutes, and then performed mild physical exercise (walking around) for another 30 min.

A PFT and an oral interview were performed thereafter. Another interview was performed 24 hours later.

Immediate Effect Results

Four of the six patients had an improvement in their pulmonary function (FEV1 AND FVC).

The improvement in FEV1 ranged between about 7% and about 25% !!!.

For two of the six there was no change in PFT. There was no change of function for the person with normal PFT.

In the first interview, ease of use was affirmed by all participants. None reported any immediate side effect. Some reported increased well being and mucus secretion immediately.

24 Hours after the Treatment Interview

Most of the patients had a better general well being feeling. Specifically, they felt;
Improvement of ease of breathing,
Less shortness of breath,
Increased sputum production.

TABLE 1

Therapeutic Protocols for Asthma, COPD and CF

| Disease | Step number | Frequency, Hz | Rpm of rotating disc | Duration, min | Remarks |
|---|---|---|---|---|---|
| Asthma | 1 | 60.0 ± 7.0 | 3600 ± 360 | 1.0 ± 0.1 | — |
|  | 2 | 8.0 ± 0.9 | 480 ± 48 | 1.5 ± 0.15 | — |
|  | 3 | 5.0 ± 0.6 | 300 ± 30 | 1.5 ± 0.15 | — |
|  | 4 | 25.0 ± 3.0 | 1500 ± 150 | 2.5 ± 0.25 | — |
|  | 5 | 0 | 0 | 1.0 ± 0.1 | Rest |
|  | 6 | 13.0 ± 7.0 | 780 ± 78 | 1.5 ± 0.15 | — |
|  | 7 | 7.0 ± 7.0 | 720 ± 72 | 1.5 ± 0.15 | — |
|  | 8 | 0 | 0 | 1.0 ± 0.1 | Rest |
|  | 9 | 34.0 ± 7.0 | 2040 ± 204 | 2.5 ± 0.25 | — |
|  | 10 | 19.0 ± 7.0 | 1140 ± 114 | 3.0 ± 0.3 | — |
|  | Total |  |  | 17 | — |
| COPD | 1 | 60.0 ± 7.0 | 3600 ± 360 | 0.5 ± 0.05 | — |
|  | 2 | 5.0 ± 0.6 | 300 ± 30 | 3.0 ± 0.3 | — |
|  | 3 | 7.0 ± 7.0 | 438 ± 42 | 2.0 ± 0.2 | — |
|  | 4 | 0 | 0 | 1.0 ± 0.1 | Rest |
|  | 5 | 13.0 ± 7.0 | 780 ± 78 | 3.0 ± 0.3 | — |
|  | 6 | 34.0 ± 7.0 | 2040 ± 204 | 2.0 ± 0.2 | — |
|  | 7 | 0 | 0 | 1.0 ± 0.1 | Rest |
|  | 8 | 5.0 ± 0.6 | 300 ± 30 | 2.0 ± 0.2 | — |
|  | 9 | 13.0 ± 7.0 | 780 ± 78 | 2.0 ± 0.2 | — |
|  | 10 | 25.0 ± 3.0 | 1500 ± 150 | 2.0 ± 0.2 | — |
|  | Total |  |  | 18.5 | — |
| CF | 1 | 60.0 ± 7.0 | 3600 ± 360 | 0.5 ± 0.5 | — |
|  | 2 | 10.0 ± 7.0 | 600 ± 60 | 2.0 ± 0.2 | — |
|  | 3 | 5.0 ± 0.6 | 300 ± 30 | 3.0 ± 0.3 | — |
|  | 4 | 0 | 0 | 1.0 ± 0.1 | Rest |
|  | 5 | 7.0 ± 7.0 | 438 ± 42 | 2.0 ± 0.2 | — |
|  | 6 | 13.0 ± 7.0 | 780 ± 78 | 2.0 ± 0.2 | — |
|  | 7 | 0 | 0 | 1.0 ± 0.1 | Rest |
|  | 8 | 5.0 ± 0.6 | 300 ± 30 | 3.0 ± 0.3 | — |
|  | 9 | 34.0 ± 7.0 | 2040 ± 204 | 2.0 ± 0.2 | — |
|  | 10 | 34.0 ± 7.0 | 1080 ± 108 | 3.0 ± 0.3 | — |
|  | Total |  |  | 19.5 | — |

The invention claimed is:

1. An air delivery device (ADD) configured for applying fluid pressure pulses (FPP) to a mouth of a patient comprising:
   a. an air blower for applying an air flow to a pressure chamber via a first opening;
   b. an airflow occluding means (AOM) said AOM in fluid communication with said pressure chamber is located between said first opening and a second opening of said pressure chamber;
   c. a respiratory mask in fluid communication with said second opening and attachable to the mouth of said patient and applying said FPP at the mouth of said patient during inspiration and expiration of said patient said respiratory mask is selected from a group consisting of a patient mouthpiece and a Face Mask, and
   d. a control unit configured for controlling said AOM, wherein said AOM comprises a fixed disc and a rotary disc; said fixed disc and said rotary disc are cooperatively configured to interrupt and release said airflow at a predetermined variable frequency and pressure thereby generating said FPP according to a predetermined protocol during operation of said ADD.

2. The ADD according to claim 1, wherein said predetermined protocol is selected from a table consisting of:

| Disease | Step number | Frequency, Hz | Rpm of rotating disc | Duration, min | Remarks |
|---|---|---|---|---|---|
| Asthma | 1 | 60.0 ± 7.0 | 3600 ± 360 | 1.0 ± 0.1 | — |
| | 2 | 8.0 ± 0.9 | 480 ± 48 | 1.5 ± 0.15 | — |
| | 3 | 5.0 ± 0.6 | 300 ± 30 | 1.5 ± 0.15 | — |
| | 4 | 25.0 ± 3.0 | 1500 ± 150 | 2.5 ± 0.25 | — |
| | 5 | 0 | 0 | 1.0 ± 0.1 | Rest |
| | 6 | 13.0 ± 7.0 | 780 ± 78 | 1.5 ± 0.15 | — |
| | 7 | 7.0 ± 7.0 | 720 ± 72 | 1.5 ± 0.15 | — |
| | 8 | 0 | 0 | 1.0 ± 0.1 | Rest |
| | 9 | 34.0 ± 7.0 | 2040 ± 204 | 2.5 ± 0.25 | — |
| | 10 | 19.0 ± 7.0 | 1140 ± 114 | 3.0 ± 0.3 | — |
| | Total | | | 17 | — |
| Chronic Obstructive Pulmonary Disease (COPD) | 1 | 60.0 ± 7.0 | 3600 ± 360 | 0.5 ± 0.05 | — |
| | 2 | 5.0 ± 0.6 | 300 ± 30 | 3.0 ± 0.3 | — |
| | 3 | 7.0 ± 7.0 | 438 ± 42 | 2.0 ± 0.2 | — |
| | 4 | 0 | 0 | 1.0 ± 0.1 | Rest |
| | 5 | 13.0 ± 7.0 | 780 ± 78 | 3.0 ± 0.3 | — |
| | 6 | 34.0 ± 7.0 | 2040 ± 204 | 2.0 ± 0.2 | — |
| | 7 | 0 | 0 | 1.0 ± 0.1 | Rest |
| | 8 | 5.0 ± 0.6 | 300 ± 30 | 2.0 ± 0.2 | — |
| | 9 | 13.0 ± 7.0 | 780 ± 78 | 2.0 ± 0.2 | — |
| | 10 | 25.0 ± 3.0 | 1500 ± 150 | 2.0 ± 0.2 | — |
| | Total | | | 18.5 | — |
| Cystic Fibrosis (CF) | 1 | 60.0 ± 7.0 | 3600 ± 360 | 0.5 ± 0.5 | — |
| | 2 | 10.0 ± 7.0 | 600 ± 60 | 2.0 ± 0.2 | — |
| | 3 | 5.0 ± 0.6 | 300 ± 30 | 3.0 ± 0.3 | — |
| | 4 | 0 | 0 | 1.0 ± 0.1 | Rest |
| | 5 | 7.0 ± 7.0 | 438 ± 42 | 2.0 ± 0.2 | — |
| | 6 | 13.0 ± 7.0 | 780 ± 78 | 2.0 ± 0.2 | — |
| | 7 | 0 | 0 | 1.0 ± 0.1 | Rest |
| | 8 | 5.0 ± 0.6 | 300 ± 30 | 3.0 ± 0.3 | — |
| | 9 | 34.0 ± 7.0 | 2040 ± 204 | 2.0 ± 0.2 | — |
| | 10 | 34.0 ± 7.0 | 1080 ± 108 | 3.0 ± 0.3 | — |
| | Total | | | 19.5 | —. |

3. The ADD according to claim 1, wherein said pressure chamber is additionally provided with a fluid supplied by a fluid source and a fluid vibrating means (GFVM), said fluid source and said GFVM are located between said AOM and said second opening and said GFVM is adapted to vibrate said fluid supplied by said fluid source at an inlet of said GFVM in said chamber at said predetermined variable frequency and pressure and providing vibrationally modulated FPP at the mouth of said patient.

4. The ADD according to claim 2, wherein pressure of said FPP is selected from a group consisting of FPP pressures which are greater than ambient fluid pressure and FPP pressures which are less than the ambient fluid pressure.

5. The ADD according to claim 3, wherein said fluid is a pharmaceutically acceptable material and said pharmaceutically acceptable material is selected from a group consisting of air, oxygen, nitrogen, nitrous-oxide, carbon dioxide, noble gases, medicament-enriched fluid or fluids, anesthetic-enriched fluid or fluids, particles, salt crystals, fine particles, nano-particles, fillers, flowing matter, ice-crystals liposomes, vesicles, thickifiers, thickeners, mucus viscosity decreasing agents, mucus viscosity increasing agents, fine particles from any plant or microorganism source; genetically modified DNA, biological vectors containing genetically modified DNA, antibodies, proteins, peptides, enzymes, hormones, factors, co-factors, carbohydrates, glycoprotein's, lipoproteins, water-immiscible materials and any combination thereof.

6. The ADD according to claim 1, said ADD further comprises means for providing said FPP directly to the respiratory system of said patient via a respiratory pipe said respiratory pipe is selected from a group consisting of a laryngoscope and a nasal-cannula.

7. The ADD according to claim 1, said ADD further comprises at least one sensor measuring at least one respiratory parameter selected from a group consisting of Forced Vital Capacity, Forced Expiratory Volume in 1 Second, Peak Expiratory Flow, Forced Expiratory Flow in ranges of 25-75% or 25-50%, Forced Inspiratory Flow in ranges of 25%-75% or 25%-50%, Forced Expiratory Time, Slow Vital capacity, Tidal Volume, Maximum Voluntary Ventilation.

8. The ADD according to claim 7, wherein said at least one sensor is adapted to generate an electrical signal corresponding to a detected airflow in said patient's airways said at least one sensor comprises at least one transducer adapted to detect an acoustic wave and to transmit a corresponding electrical signal to an analyzing means.

9. The ADD according to claim 1, wherein said ADD is adapted for continuous positive airway pressure (CPAP) therapy and is integrated and embedded in an air delivery member said air delivery member is selected from a group consisting of CPAP device, said mouthpiece and a respiratory pipe of said patient.

10. A method configured for applying air pressure pulses (FPP) to a mouth cavity of a patient; said method for applying air pressure pulses (FPP) to a mouth cavity of a patient comprising steps of:

a. providing an air delivery device (ADD), said ADD comprising:

i. an air blower for applying an airflow to a pressure chamber via an inlet; said pressure chamber comprises an air vibrating means (AVM) for vibrating air contained in said pressure chamber at a predetermined variable frequency and pressure and providing a vibrationally modulated FPP to the mouth cavity of said patient pressure of said vibrationally modulated FPP is selected from a group consisting of air pressure greater than ambient air pressure and air pressure less than ambient air pressure;

ii. an airflow occluding means (AOM) in fluid communication with said pressure chamber said AOM interrupting and releasing said airflow at said predetermined variable frequency and pressure and said AOM is located between said inlet and an outlet of said pressure chamber; a respiratory mask air delivery member in fluid communication with said outlet said respiratory mask air delivery member is selected from a group consisting of a respiratory pipe and a mouthpiece, and iii. a control unit preprogrammed for providing pneumatic pulses according to a therapeutic protocol, b. applying said vibrationally modulated FPP at the predetermined variable frequency and pressure to the mouth cavity of said patient according to said therapeutic protocol;

wherein said AOM comprises a fixed disc and a rotary disc; said discs are cooperatively configured to interrupt and release said airflow at a predetermined variable frequency and pressure thereby generating said vibrationally modulated FPP according to a predetermined protocol during operation of said ADD, and wherein said therapeutic protocol comprises:

| Disease | Step number | Frequency, Hz | Rpm of rotating disc | Duration, min | Remarks |
|---|---|---|---|---|---|
| Asthma | 1 | 60.0 ± 7.0 | 3600 ± 360 | 1.0 ± 0.1 | — |
| | 2 | 8.0 ± 0.9 | 480 ± 48 | 1.5 ± 0.15 | — |
| | 3 | 5.0 ± 0.6 | 300 ± 30 | 1.5 ± 0.15 | — |
| | 4 | 25.0 ± 3.0 | 1500 ± 150 | 2.5 ± 0.25 | — |
| | 5 | 0 | 0 | 1.0 ± 0.1 | Rest |
| | 6 | 13.0 ± 7.0 | 780 ± 78 | 1.5 ± 0.15 | — |
| | 7 | 7.0 ± 7.0 | 720 ± 72 | 1.5 ± 0.15 | — |
| | 8 | 0 | 0 | 1.0 ± 0.1 | Rest |
| | 9 | 34.0 ± 7.0 | 2040 ± 204 | 2.5 ± 0.25 | — |
| | 10 | 19.0 ± 7.0 | 1140 ± 114 | 3.0 ± 0.3 | — |
| | Total | | | 17 | — |
| Chronic Obstructive Pulmonary Disease (COPD) | 1 | 60.0 ± 7.0 | 3600 ± 360 | 0.5 ± 0.05 | — |
| | 2 | 5.0 ± 0.6 | 300 ± 30 | 3.0 ± 0.3 | — |
| | 3 | 7.0 ± 7.0 | 438 ± 42 | 2.0 ± 0.2 | — |
| | 4 | 0 | 0 | 1.0 ± 0.1 | Rest |
| | 5 | 13.0 ± 7.0 | 780 ± 78 | 3.0 ± 0.3 | — |
| | 6 | 34.0 ± 7.0 | 2040 ± 204 | 2.0 ± 0.2 | — |
| | 7 | 0 | 0 | 1.0 ± 0.1 | Rest |
| | 8 | 5.0 ± 0.6 | 300 ± 30 | 2.0 ± 0.2 | — |
| | 9 | 13.0 ± 7.0 | 780 ± 78 | 2.0 ± 0.2 | — |
| | 10 | 25.0 ± 3.0 | 1500 ± 150 | 2.0 ± 0.2 | — |
| | Total | | | 18.5 | — |
| Cystic Fibrosis (CF) | 1 | 60.0 ± 7.0 | 3600 ± 360 | 0.5 ± 0.5 | — |
| | 2 | 10.0 ± 7.0 | 600 ± 60 | 2.0 ± 0.2 | — |
| | 3 | 5.0 ± 0.6 | 300 ± 30 | 3.0 ± 0.3 | — |
| | 4 | 0 | 0 | 1.0 ± 0.1 | Rest |
| | 5 | 7.0 ± 7.0 | 438 ± 42 | 2.0 ± 0.2 | — |
| | 6 | 13.0 ± 7.0 | 780 ± 78 | 2.0 ± 0.2 | — |
| | 7 | 0 | 0 | 1.0 ± 0.1 | Rest |
| | 8 | 5.0 ± 0.6 | 300 ± 30 | 3.0 ± 0.3 | — |
| | 9 | 34.0 ± 7.0 | 2040 ± 204 | 2.0 ± 0.2 | — |
| | 10 | 34.0 ± 7.0 | 1080 ± 108 | 3.0 ± 0.3 | — |
| | Total | | | 19.5 | —. |

11. A predetermined protocol adapted for applying fluid pressure pulses (FPP) to a mouth cavity of a patient by means of an air delivery device (ADD), said ADD comprising:
  a. a pressure chamber having a first opening and a second opening;
  b. an air blower applying air into said pressure chamber via the first opening;
  c. an airflow occluding means (AOM) provided in fluid communication with said pressure chamber, said AOM located between said first opening and a second opening of said pressure chamber;
  d. a patient mouthpiece, in fluid communication with said second opening; and
  e. a control unit,
wherein said AOM comprises a fixed disc and a rotary disc; said discs are cooperatively configured to interrupt and release said airflow at a predetermined variable frequency and pressure thereby generating said FPP according to the predetermined protocol during operation of said ADD, and wherein said predetermined protocol is selected according to a patient's indications from a table consisting of:

| Disease | Step number | Frequency, Hz | Rpm of rotating disc | Duration, min | Remarks |
|---|---|---|---|---|---|
| Asthma | 1 | 60.0 ± 7.0 | 3600 ± 360 | 1.0 ± 0.1 | — |
| | 2 | 8.0 ± 0.9 | 480 ± 48 | 1.5 ± 0.15 | — |
| | 3 | 5.0 ± 0.6 | 300 ± 30 | 1.5 ± 0.15 | — |
| | 4 | 25.0 ± 3.0 | 1500 ± 150 | 2.5 ± 0.25 | — |
| | 5 | 0 | 0 | 1.0 ± 0.1 | Rest |
| | 6 | 13.0 ± 7.0 | 780 ± 78 | 1.5 ± 0.15 | — |
| | 7 | 7.0 ± 7.0 | 720 ± 72 | 1.5 ± 0.15 | — |
| | 8 | 0 | 0 | 1.0 ± 0.1 | Rest |
| | 9 | 34.0 ± 7.0 | 2040 ± 204 | 2.5 ± 0.25 | — |
| | 10 | 19.0 ± 7.0 | 1140 ± 114 | 3.0 ± 0.3 | — |
| | Total | | | 17 | — |
| Chronic Obstructive Pulmonary Disease (COPD) | 1 | 60.0 ± 7.0 | 3600 ± 360 | 0.5 ± 0.05 | — |
| | 2 | 5.0 ± 0.6 | 300 ± 30 | 3.0 ± 0.3 | — |
| | 3 | 7.0 ± 7.0 | 438 ± 42 | 2.0 ± 0.2 | — |
| | 4 | 0 | 0 | 1.0 ± 0.1 | Rest |
| | 5 | 13.0 ± 7.0 | 780 ± 78 | 3.0 ± 0.3 | — |
| | 6 | 34.0 ± 7.0 | 2040 ± 204 | 2.0 ± 0.2 | — |
| | 7 | 0 | 0 | 1.0 ± 0.1 | Rest |
| | 8 | 5.0 ± 0.6 | 300 ± 30 | 2.0 ± 0.2 | — |
| | 9 | 13.0 ± 7.0 | 780 ± 78 | 2.0 ± 0.2 | — |
| | 10 | 25.0 ± 3.0 | 1500 ± 150 | 2.0 ± 0.2 | — |
| | Total | | | 18.5 | — |
| Cystic Fibrosis (CF) | 1 | 60.0 ± 7.0 | 3600 ± 360 | 0.5 ± 0.5 | — |
| | 2 | 10.0 ± 7.0 | 600 ± 60 | 2.0 ± 0.2 | — |
| | 3 | 5.0 ± 0.6 | 300 ± 30 | 3.0 ± 0.3 | — |
| | 4 | 0 | 0 | 1.0 ± 0.1 | Rest |
| | 5 | 7.0 ± 7.0 | 438 ± 42 | 2.0 ± 0.2 | — |
| | 6 | 13.0 ± 7.0 | 780 ± 78 | 2.0 ± 0.2 | — |
| | 7 | 0 | 0 | 1.0 ± 0.1 | Rest |
| | 8 | 5.0 ± 0.6 | 300 ± 30 | 3.0 ± 0.3 | — |
| | 9 | 34.0 ± 7.0 | 2040 ± 204 | 2.0 ± 0.2 | — |
| | 10 | 34.0 ± 7.0 | 1080 ± 108 | 3.0 ± 0.3 | — |
| | Total | | | 19.5 | —. |

\* \* \* \* \*